United States Patent [19]

Colombo et al.

[11] 4,340,731
[45] Jul. 20, 1982

[54] POLYCARBOXYALKYL-CELLULOSE HAVING HIGH FLUID ABSORBING AND RETAINING PROPERTIES, AND PROCESS FOR PREPARING SAME

[75] Inventors: Virginio Colombo, Melzo; Alberto Nicoletti; Benito Casu, both of Milan, all of Italy

[73] Assignee: Montedison S.p.A., Milan, Italy

[21] Appl. No.: 160,990

[22] Filed: Jun. 19, 1980

[30] Foreign Application Priority Data

Jun. 20, 1979 [IT] Italy ............................... 23716 A/79

[51] Int. Cl.³ .................... C08B 11/12; C08B 11/20
[52] U.S. Cl. ...................................... 536/87; 128/156; 128/290 R; 536/88; 536/97; 536/98
[58] Field of Search ................... 536/87, 88, 97, 98; 106/197 C

[56] References Cited

U.S. PATENT DOCUMENTS

| | | | |
|---|---|---|---|
| 2,523,377 | 9/1950 | Klug | 536/98 |
| 2,639,239 | 5/1953 | Elliott | 106/197 C |
| 3,379,721 | 4/1968 | Reid | 106/197 C |
| 3,589,364 | 6/1971 | Dean | 128/285 |
| 3,678,031 | 7/1972 | Schoggen | 106/197 C |
| 3,723,413 | 3/1973 | Chatterjee et al. | 536/87 |
| 3,728,331 | 4/1973 | Savage | 536/88 |
| 3,731,686 | 5/1973 | Chatterjee | 128/285 |
| 4,200,557 | 4/1980 | Chatterjee et al. | 128/285 |
| 4,200,736 | 4/1980 | Shinohara et al. | 536/98 |
| 4,200,737 | 4/1980 | Marder et al. | 536/98 |
| 4,248,595 | 2/1981 | Lask et al. | 536/87 |

FOREIGN PATENT DOCUMENTS

| | | | |
|---|---|---|---|
| 937480 | 10/1971 | Italy . | |
| 953944 | 4/1964 | United Kingdom | 536/88 |
| 1086323 | 10/1967 | United Kingdom | 536/98 |

*Primary Examiner*—Ronald W. Griffin

[57] ABSTRACT

Polycarboxyalkyl-cellulose characterized by exceptionally high fluid absorbing and retaining capacities is obtained by oxidizing, under particular conditions, hydroinsoluble, cross-linked carboxyalkyl-cellulose having a substitution degree greater than 0.35.

7 Claims, No Drawings

POLYCARBOXYALKYL-CELLULOSE HAVING HIGH FLUID ABSORBING AND RETAINING PROPERTIES, AND PROCESS FOR PREPARING SAME

THE PRIOR ART

As is known, for the preparation of absorbent materials capable of retaining fluids, in general, cotton, rayon, wood pulp and other similar cellulosic materials are used.

In order to improve the absorbing power of such materials it has been suggested to carboxy-alkylate them.

The carboxyalkyl-ethers of cellulose which may, however, be used in practice, are those having a substitution degree (S.D.) corresponding to a maximum of 0.35 carboxyalkyl radicals per unit of anhydroglucose. In fact, when the degree of substitution exceeds 0.35, the carboxyalkyl-cellulose tends to become too soluble in water.

Various processes have been suggested for rendering carboxyalkyl-cellulose having a substitution degree greater then 0.35 insoluble in water.

Thus, for instance, U.S. Pat. No. 3,589,364 discloses a process for insolubilizing carboxymethyl-cellulose, which usually is soluble in water, by cross-linking with epichlorohydrin, so as to form highly absorbent products.

According to U.S. Pat. Nos. 2,639,239 and 3,731,686; British Pat. No. 1,086,323 and Italian Pat. No. 937,480, carboxyalkyl-cellulose having a substitution degree greater than 0.35, may be made practically insoluble in water and highly absorbent by heat-treatment in the form of its sodium salt.

The products obtained by said processes display, however, the unwanted characteristic of showing a pronounced drop in their absorbing and retaining capacity when passing from distilled water to saline solutions.

THE PRESENT INVENTION

One object of this invention is that of obtaining a carboxyalkyl-cellulose that is practically hydroinsoluble, that has a substitution degree greater than 0.35, and that possesses a high absorption and retention power or capacity, both towards water as well as towards saline solutions, and likewise towards physiological and plasmatic liquids.

This and other objects which will appear to those skilled in the art from the disclosures hereinafter are achieved by this invention in accordance with which it has been found that by subjecting hydroinsoluble cross-linked carboxyalkyl-cellulose to oxidation, a substantially hydroinsoluble, cross-linked and oxidized carboxyalkyl-cellulose is obtained having much higher absorption and retention powers, both for water as well as for saline solutions or physiological and plasmatic liquids, as well as a lower pH value.

The term "substantially hydroinsoluble", as used herein, means a polycarboxyalkylated cellulosic material having a hydrosolubility (in water) of less than 40% by weight, and preferably at least 15% by weight.

By the process of this invention, therefore, there is obtained a polycarboxyalkyl-cellulose having a substitution degree greater than 0.35, a cross-linking comprised between 5% and up to 75% of the substituted groups, a hydrosolubility of less than 40% by weight, an absorption and retention of the water of between 7,000 and 25,000 ml/100 g of pure product, an absorption and retention of saline solutions or physiological and plasmatic liquids comprised between 2,500 and 6,000 ml/100 g of pure product, and a pH value of less than 6.5.

For the practical embodiment of the process for the preparation of the cross-linked and oxidized carboxyalkyl-cellulose of the above reported properties, the cellulose in the form of fibers, small squares, flakes or powder, is dispersed in an organic inert diluent, such as, for instance, isopropanol, ethanol, benzene, acetone, ter.-butanol, etc., in a nitrogen atmosphere completely free of air, and with a total liquid/cellulose ratio comprised between 1.5:1 and 3.5:1, but preferably comprised between 2.5:1 and 3:1.

The cellulose dispersed in the diluent is then brought into contact with an alkaline metal hydroxide, such as sodium hydroxide, potassium hydroxide or lithium hydroxide, so as to form the alkali-cellulose.

The alkali-cellulose thus obtained is etherified by a treatment with an etherification agent, which may be, for example, monochloroacetic acid, monochloropropionic acid, etc.

The degree of substitution obtained during the etherification is such as to render the corresponding carboxyalkyl-cellulose soluble in water, and more particularly said degree of substitution is comprised between 0.4 and 1.5.

The quantity of etherification agent to be used may vary within very wide ranges, even though, in practice, it is presently preferred to operate with 0.5–2.2 mols, more preferably with from 1.2 to 1.4 mols of etherification agent per mol of anhydroglucosidic unit.

The quantity of alkaline metal hydroxide is adjusted or regulated depending on the etherification agent, and in general is comprised between 1.7 and 1.9 mols/mol of etherification agent.

For the preparation of the alkali-cellulose, the suspension consisting of cellulose, inert organic diluent and of an alkaline metal hydroxide, having a water/cellulose ratio comprised between 0.5:1 and 1:1 and an organic diluent/water ratio comprised between 2:1 and 3:1, is maintained at a temperature of 0°–50° C., and preferably comprised between 20° and 30° C., for a period of time preferably comprised between 30 and 60 minutes.

The alkali-cellulose thus obtained is reacted with the etherification agent, preferably monochloroacetic acid, in the above indicated quantities, at a temperature comprised between 50° and 90° C., and preferably between 70° and 75° C., and for a period of about 30 to 90 minutes. The times and temperatures of the reaction are chosen out of the above reported ranges in order to obtain a salt of an alkaline metal of the carboxyalkyl-cellulose that is substantially soluble in water and having a degree of substitution of about 0.4–1.5. From the reaction suspension, the organic diluent may then be removed by operating under reduced pressure and at a temperature comprised between 45° and 60° C.

After removal of the diluent, the carboxyalkyl-cellulose thus obtained is subjected to a heat-treatment at a temperature comprised between 85° and 115° C., but preferably between 95° and 105° C., for a period of time of between 30 and 120 minutes, so as to achieve the internal cross-linking of the carboxyalkyl-cellulose, and thus make it practically insoluble in water.

According to British Pat. No. 1,086,323, the heat-treatment to render the carboxyalkyl-cellulose hydroinsoluble must be carried out at a pH value between 4.5 and 5.5. Such pH values may be obtained either operating with an excess of etherification agent during the etherification process, or by the addition of an inorganic acid such as hydrochloric acid, sulphuric acid, etc., or of a strong organic acid, so as to free acid carboxylic groups.

According to this invention, the hydroinsoluble carboxyalkyl-cellulose, obtained by internal heat-crosslinking, is treated with an oxidizing agent, at a temperature of between 0° and 80° C., and preferably at between 20° and 50° C., and for a time period comprised between 30 minutes and 24 hours.

As oxidizing agents there may be used either organic or inorganic compounds such as for instance: sodium periodate-bromine water, tetraacetate lead-bromine water, hydrogen peroxide, organic peroxides such as peresters, peroxyketals, etc.

Of the above listed oxidizing agents, the presently preferred one is hydrogen peroxide inasmuch as it allows to obtain the desired oxidation in appreciably short times, such as between 30 and 90 minutes.

The oxidation product thus obtained shows a pH value below 6.5 and preferably comprised between 5.5 and 6.4 which is decidedly lower than that of the non-oxidized starting product.

By considering that such an increase of acidity is due to free acid groups, the oxidized product has been given the name of polycarboxyalkyl-cellulose.

For the determination of the properties of the polycarboxyalkyl-cellulose obtained according to the process of this invention, the following methods have been used:

Determination of the absorption and retention of water (VRA)

0.05–0.3 grams of samples of polycarboxyalkyl-cellulose are immersed in and imbibed with 100 ml of distilled water, in a closed container, for at least 16 hours at room temperature.

The fibers thus impregnated with water are gathered by filtering, slightly squeezed and then placed into pipes having bottoms formed by a 75 mesh net.

The pipes are then placed into a centrifuge in place of the test tubes, and the samples are then centrifuged at a relative centrifugal force of between 1,500 and 1,700 gravity, for 20 minutes.

The centrifuged samples are thereupon rapidly removed from the pipes of the centrifuge, by means of tweezers, and transferred to calibrated weighing bottles in which they are then weighed. The weighed samples are dried at constant weight at a temperature of 110° C., and then weighed again.

The water absorption and retention value (VRA) is determined by the equation:

$$VRA = \frac{W - D}{D} \times 100$$

wherein:
W = weight of humid sample
D = weight of dry sample
W − D = weight of absorbed water.

Determination of the absorption and retention of saline solutions (VRS)

The method for the determination of the absorption and retention of saline solutions is analogous to that for the determination of the absorption and retention of water, except that, instead of distilled water, there is used a 1% b.w. solution of NaCl. Moreover, in the formula for the determination of the quantity of absorbed and retained solution, there must be taken into account the sodium chloride that remains on the dried fibers.

Thus, the formula is:

$$VRS = \frac{W - D\left(\frac{100}{99}\right)}{\frac{W-D}{99}} \times 100$$

wherein: W and D have the same meaning as in the VRA equation.

Measure of the pH

The pH value is measured on the 1% b.w. aqueous suspension of the product.

Measure of the solubility in water 0.2–0.3 grams of the product are washed in a beaker and are then immersed for a prolonged period of time (12–16 hours) in 100 ml of water containing 1% of NaCl.

The water-impregnated fibers are gathered in a calibrated crucible, are wet-weighed, dried at 110° C. and finally weighed again. The quantity of soluble product is given by the formula:

$$\% \text{ of soluble prod.} = 100 - \frac{E - \frac{W-E}{99}}{B} \times 100$$

wherein:
B = initial weight of dry sample,
W = weight of humid sample,
E = final weight of dry sample.

Determination of the degree of substitution

The determination of the degree of substitution was carried out according to the method described in "Svensk Papperstidning" 63 (1960), pages 714–715, by Karin Wilson, modified in the sense that there is used methyl alcohol instead of ethyl alcohol.

The following examples are given for a better understanding of the inventive concept of this invention and as enabling for the practice thereof, and are not intended to be limiting.

EXAMPLE 1

4,000 g of cellulose fibers containing 5% of water were introduced into a reactor and, after eliminating all of the air present in it by means of nitrogen, were additioned with 8000 g of isopropanol containing 13% of $H_2O$.

Again, possible traces of oxygen still present in the reactor were eliminated, and to the suspension there were rapidly added 3,722 grams of aqueous sodium hydroxide at 50.6% concentration. The suspension was then allowed to mercerize for 30 minutes at temperatures of between 20° C. and 30° C., in order to complete the formation of alkali-cellulose.

At the end of the mercerization, there were slowly added 2,214 grams of monochloroacetic acid, pre-dissolved in 530 g of $H_2O$ and 1700 g of azeotropic isopropanol (water content = 13%).

The suspension was then heated up to 80° C. and maintained at that temperature for a period of 40 minutes, so as to form hydrosoluble carboxymethyl-cellulose. The isopropanol was recovered by distillation, and the carboxymethyl-cellulose was cooled down to 45° C., whereupon there were introduced 1,368 g of aqueous HCl at 10% concentration.

The suspension was then heated up to 95° C. and maintained at that temperature for 60 minutes.

About 500 g of cross-linked carboxymethyl-cellulose were drawn from the reactor and suspended in a flask with about 4,000 g of water.

To the suspension was then added, under stirring, in a nitrogen atmosphere and at a constant temperature of about 35° to 40° C., an aqueous solution containing 7.64 g (0.0357 mol) of sodium periodate.

The reaction was carried out in the dark for 24 hours. At the end of the reaction, the carboxymethyl-cellulose was filtered, suspended in about 2,000 g of water and this suspension was then additioned with 11.57 g of bromine in water, by means of a dripper.

The mixture was then allowed to rest for 8 hours, after which it was concentrated under vacuum. Methanol was added in order to render the polycarboxymethyl-cellulose thus obtained more readily filterable. After filtering, the whole was dried in an oven at 70° C.

The pure polycarboxymethyl-cellulose thus obtained showed the following characteristics:
 VRA = 8412 ml/100 g of product
 VRS = 2732 ml/100 g of product
 pH value = 6.3
 Solubility = 38.24%

EXAMPLE 2

Example 1 was repeated except that the oxidation under nitrogen atmosphere was carried out with tetraacetate-lead and bromine water. More particularly, 500 g of cross-linked carboxymethyl-cellulose were dispersed in 4,000 g of water and were then additioned with a solution containing 14.77 g (0.0333 mol) of tetraacetate-lead, maintaining the temperature between 35° and 40° C.

After 24 hours, the carboxymethyl-cellulose was filtered, suspended in about 2,000 g of water and finally treated with 10.65 g of bromine in water.

The pure polycarboxymethyl-cellulose thus obtained, separated and dried as in Example 1, had the following characteristics:
 VRA = 9200 ml/100 g of product
 VRS = 2800 ml/100 g of product
 pH value = 6.4
 Solubility = 35%.

EXAMPLE 3

Into a 50 lt reactor, from which all the air had been removed by means of nitrogen, there were introduced 4,000 g of cellulose fibers containing 5% by weight of water, and 8,000 g of azeotropic isopropanol alcohol (water content = 13%).

To the suspension there were rapidly added, under stirring, 4,100 g of aqueous sodium hydroxide at 50.6% b.w. and the suspension was then allowed to mercerize for 30 minutes at a temperature of between 20° and 30° C.

Then there were added very slowly, and over a period of 40 minutes, 2,685 g of monochloroacetic acid dissolved in 672 g of water and 2,700 g of azeotropic isopropyl alcohol. The suspension was heated up to 80° C. for 40 minutes so as to form the hydrosoluble carboxymethyl-cellulose with a substitution degree equal to 0.8.

After removal of the isopropyl alcohol by means of distillation, the hydrosoluble carboxymethyl-cellulose was heated up to 95° C., and this temperature was then maintained for 60 minutes. The product, separated by filtering, repeatedly washed with aqueous methanol and then with anhydrous methanol, then dried at 80° C., showed the following characteristics:
 VRA = 2400 ml/100 g of product
 VRS = 1260 ml/100 g of product
 pH value = 6.7
 Solubility = 12%.

The pure product, after treatment with 300 g of aqueous $H_2O_2$ at 10% b.w. concentration, at 45° C. for 50 minutes, showed the following characteristics:
 VRA = 10,000 ml/100 g of product
 VRS = 3218 ml/100 g of the product
 pH value = 6.1
 Solubility = 31%.

If the treatment time is increased to 120 minutes, the product obtained shows the following characteristics:
 VRA = 12,000 ml/100 g of the product
 VRS = 6,600 ml/100 g of the product
 pH value = 5.6
 Solubility = 37%.

EXAMPLE 4

Example 3 was repeated except that 4,000 g of cellulose were treated with the quantities of isopropanol, of sodium hydroxide at 50% b.w. concentration, of monochloroacetic acid at 80% b.w. concentration, of hydrogen peroxide at 58% b.w. concentration, and for period of time reported in the following Table.

TABLE

| Isopropanol g | NaOH g | Monochloroacetic acid in g | $H_2O_2$ g | Oxidation time minutes | VRA | VRS | pH | Solubility % |
|---|---|---|---|---|---|---|---|---|
| 10,000 | 4,494 | 4,006 | 100 | 120 | 7,340 | 2,880 | 5.5 | 29.18 |
| 8,000 | 4,100 | 3,358 | 100 | 90 | 13,000 | 4,417 | 5.8 | 39.03 |
| 8,000 | 4,100 | 3,358 | 100 | 75 | 12,930 | 3,723 | 5.83 | 33.76 |
| 8,000 | 4,100 | 3,358 | 100 | 45 | 11,970 | 2,534 | 5.92 | 28.54 |
| 10,000 | 3,753 | 3,395 | 100 | 120 | 12,776 | 2,547 | 5.59 | 28.12 |

Due to their peculiar and distinguishing characteristics, the cellulosic products of this invention are particularly suitable for use in sanitary towels or napkins, bandages, tampons, and the like.

What is claimed is:

1. Polycarboxyalkyl-cellulose having a degree of substitution greater than 0.35, a cross-linkage comprised between 5% and up to 75% of the substituted groups, a water-solubility below 40% by weight, an absorption and retention of the water comprised between 7,000 and 25,000 ml/100 g of pure product, an absorption and retention of saline solutions or of plasmatic and physiological liquids comprised between 2,500 and 6,000 ml/100 g of pure product, and a pH between 5.5 and 6.4.

2. Process for increasing the absorption and retention power for water, saline solutions, and physiological and plasmatic liquids, of cross-linked, hydroinsoluble carboxyalkyl-cellulose, and lowering the pH value, which process consists in subjecting the cross-linked, hydroinsoluble carboxyalkyl-cellulose to an oxidizing process at a temperature below 80° C.

3. The process of claim 2, in which the oxidizing agent is sodium periodate and bromine water.

4. The process of claim 2, in which the oxidizing agent is hydrogen peroxide.

5. The process of claim 2, in which the oxidizing agent is lead tetraacetate and bromine water.

6. The process of claim 2, in which the oxidizing agent is an organic peroxide.

7. The process of claim 2, in which the cross-linked hydroinsoluble carboxyalkyl-cellulose is obtained by heat-treating hydrosoluble carboxyalkyl cellulose having a degree of substitution greater than 0.35, at a temperature comprised between 85° and 115° C., and at a pH of from 4.4 to 5.5.

* * * * *